US011978537B2

(12) United States Patent
Roy et al.

(10) Patent No.: US 11,978,537 B2
(45) Date of Patent: May 7, 2024

(54) METHOD AND SYSTEM FOR PREDICTING PROTEIN-PROTEIN INTERACTION BETWEEN HOST AND PATHOGEN

(71) Applicant: Tata Consultancy Services Limited, Mumbai (IN)

(72) Inventors: Arijit Roy, Hyderabad (IN); Dibyajyoti Das, Hyderabad (IN); Gopalakrishnan Bulusu, Hyderabad (IN)

(73) Assignee: Tata Consultancy Services Limited, Mumbai (IN)

( * ) Notice: Subject to any disclaimer, the term of this patent is extended or adjusted under 35 U.S.C. 154(b) by 842 days.

(21) Appl. No.: 16/950,407

(22) Filed: Nov. 17, 2020

(65) Prior Publication Data
US 2021/0151121 A1 May 20, 2021

(30) Foreign Application Priority Data
Nov. 18, 2019 (IN) .............................. 201921046940

(51) Int. Cl.
*G06N 20/20* (2019.01)
*G16B 5/20* (2019.01)
(Continued)

(52) U.S. Cl.
CPC ............... *G16B 5/20* (2019.02); *G06N 20/20* (2019.01); *G16B 40/00* (2019.02); *G16B 50/00* (2019.02)

(58) Field of Classification Search
CPC .......... G06N 20/20; G06N 5/02; G16B 40/00; G16B 5/20; G16B 50/00
See application file for complete search history.

(56) References Cited

FOREIGN PATENT DOCUMENTS

WO WO2016/209999 12/2016

OTHER PUBLICATIONS

"Training host-pathogen protein-protein interaction predictors" (Abstract only) Journal of Bioinformatics and Computational Biology vol. 16, No. 04, 1850014 (2018) Research Papers Abdul Hannan Basit, Wajid Arshad Abbasi, Amina Asif, Sadaf Gull, and Fayyaz Ul Amir Afsar Minhas (Year: 2018).*

(Continued)

*Primary Examiner* — Luis A Sitiriche
(74) *Attorney, Agent, or Firm* — Finnegan Henderson, Farabow, Garrett & Dunner, LLP

(57) ABSTRACT

Pathogens invade and infect humans. Understanding the infection mechanism is essential for determining targets for new therapeutics. Existing methods provide too many false positive results. A method and system for predicting protein-protein interaction between a host and a pathogen has been provided. The disclosure provides a pipeline for predicting HPIs, which is a combination of biological knowledge-based filters, domain-based filter and sequence-based predictions. Biologically feasible interactions are only possible when both the proteins share common localization and overlapping expression profiles. This observation was used as the first filter to remove biologically irrelevant HPIs. Proteins interact with each other through domains. Both interacting and non-interacting protein pairs provide valuable information about the probability of protein-protein interactions and hence both were used to derive statistical inferences to remove improbable HPIs. Finally, sequence composition of known interacting pairs of HPIs were used to train an XGBoost model and filter the most probable HPIs.

10 Claims, 5 Drawing Sheets

(51) Int. Cl.
*G16B 40/00* (2019.01)
*G16B 50/00* (2019.01)

(56) References Cited

OTHER PUBLICATIONS

J. C. Beltran, P. Valdez and P. Naval, "Predicting Protein-Protein Interactions based on Biological Information using Extreme Gradient Boosting," 2019 IEEE Conference on Computational Intelligence in Bioinformatics and Computational Biology (CIBCB), Siena, Italy, 2019 (Year: 2019).*

Soyemi, Jumoke et al., "Inter-Species/Host-Parasite Protein Interaction Predictions Reviewed" Computational approaches to solving biological related problems, 2018, NCBI, https://www.researchgate.net/publication/322374287_Inter-SpeciesHost-Parasite_Protein_Interaction_Predictions_Reviewed/link/5acf9ac54585154f3f47bd02/download.

Huo, Tong et al., "Prediction of host—pathogen protein interactions between *Mycobacterium tuberculosis* and *Homo sapiens* using sequence motifs", Bioinformatics, Mar. 2015, NCBI, https://www.researchgate.net/publication/275102166_Prediction_of_host_-_pathogen_protein_interactions_between_Mycobacterium_tuberculosis_and_Homo_sapiens_using_sequence_motifs/link/55f00a9708ae0af8ee1b5145/download.

Nourani, Esmaeil et al., "Computational approaches for prediction of pathogen-host protein-protein interactions", Frontiers in Microbiology, Feb. 2015, NCBI, https://www.researchgate.net/publication/272744222_Computational_Approaches_for_Prediction_of_Pathogen-Host_Protein-Protein_Interactions/link/5509999a0cf2d7a2812d65d8/download.

Chen, Huaming et al., "Leveraging SMOTE in A Two-Layer Model for Prediction of Protein-Protein Interactions", Seventh International Conference on Advanced Cloud and Big Data (CBD), Sep. 2019, IEEE, Link: https://ro.uow.edu.au/cgi/viewcontent.cgi?article=4273&context=eispapers1.

White Bear, Joyona et al., "Predictions of Protein-Protein Interactions in Schistosoma Mansoni", Scientific Report, Aug. 2018, NCBI, https://escholarship.org/uc/item/84h5f2z1.

* cited by examiner

METHOD AND SYSTEM FOR PREDICTING PROTEIN-PROTEIN INTERACTION BETWEEN HOST AND PATHOGEN

PRIORITY CLAIM

This U.S. patent application claims priority under 35 U.S.C. § 119 to: India Application No. 201921046940, filed on 18 Nov. 2019. The entire contents of the aforementioned application are incorporated herein by reference.

TECHNICAL FIELD

The embodiments herein generally relate to the field of study of host protein interactions. More particularly, but not specifically, the present disclosure provides a method and system for predicting protein-protein interaction between host and pathogen.

BACKGROUND

Pathogens invade and infect humans resulting in millions of deaths each year. Moreover many pathogens acquire drug resistance making several drugs obsolete. Understanding the infection mechanism is thus essential for determining targets for new therapeutics. Despite several experimental studies, knowledge about host-pathogen interactions (HPIs) is limited, but identifying the HPIs can provide a holistic understanding of the infection mechanism. This knowledge is essential to understand pathogenesis and identify potential targets for disease prevention and clinical intervention. A suitable method for HPI prediction will enable researchers to find novel mechanisms of host-pathogen protein-protein interactions which will help to identify new drugs with novel mechanisms of actions.

Knowledge about the complete pathogen invasion mechanism is inadequate and experimental research on host-pathogen interactions are limited. Large-scale experimental HPI detection like tandem affinity purification and yeast two-hybrid experiments provide a larger picture but at the cost of significant false-negative and false-positive error rates along with being expensive and time consuming. In few cases, like the malaria pathogen, *Plasmodium falciparum*, experiments are difficult due to low-complexity regions of the pathogen proteins.

In addition to that computational approaches have also been utilized to recognize and understand pathogen infection mechanisms. Computational techniques suffer from the limitations of experimentally known HPIs for a particular species. In spite of such positive-dataset scarcity, computational models are generated with either this limited number of known HPIs or use a homology based approach based on the assumption that homologous proteins preserve their ability to interact. To compensate for the lack of available HPIs, these methods also use the intra-species protein-protein interactions (PPIs) which also provides false positives. There are also attempts to predict HPIs using domain information alone without considering the frequency of domains of non-interacting protein pairs and hence suffer from false positives. Negative dataset, required to train the learning model against incorrect interacting pairs, plays a significant role in machine learning based approaches but there is no available experimental non-interacting HPI data. In many earlier studies, the negative dataset was generated from non-interacting proteins obtained from positive dataset, therefore significantly increasing the rate of false positives.

SUMMARY

Embodiments of the present disclosure present technological improvements as solutions to one or more of the above-mentioned technical problems recognized by the inventors in conventional systems. For example, in one embodiment, a system for predicting protein-protein interaction between a host and a pathogen has been provided. The system comprises a first database, a second database, one or more hardware processors and a memory in communication with the one or more hardware processors. The first database provides a positive dataset, wherein the positive dataset contains a set of known host pathogen interactions (HPIs). The second database provides a negative dataset, wherein the negative dataset contains non-interacting proteins of the host and the pathogen which are unlikely to exhibit direct physical interactions. The memory further comprises an interactions creation module, a biological knowledge based filter, a domain based statistical filter, a training module and a prediction module. The interactions creation module creates a cross of all possible interactions between a set of host proteins and a set of pathogen proteins to get an input list of host-protein interfaces (HPIs). The biological knowledge based filter applies filter on the input list to remove the pathogen proteins which are unable to interact with the host proteins, and remove the host proteins which are unable to interact with the pathogen proteins, wherein the application results in generation of a second list of HPIs. The domain based statistical filter applies filter on the second list to remove statistically irrelevant HPIs using the positive dataset and the negative dataset, wherein the application results in generation of a set of unknown HPIs. The training module trains an extreme gradient boosting (XGBoost) model using a sequence composition of interacting pairs of HPIs obtained from the positive dataset and the negative dataset. The prediction module predicts the interactions using the set of unknown HPIs and the trained XGBoost model, wherein the set of unknown HPIs are provided as input to the trained XGBoost model.

In another aspect, the embodiment here provides a method for predicting protein-protein interaction between a host and a pathogen. Initially, a positive dataset is collected from a first database, wherein the positive dataset contains a set of known host pathogen interactions (HPIs). Similarly, a negative dataset is collected from a second database, wherein the negative dataset contains non-interacting proteins of the host and the pathogen which are unlikely to exhibit direct physical interactions. In the next step, a cross of all possible interactions is created between a set of host proteins and a set of pathogen proteins to get an input list of host-protein interactions (HPIs). Further, a biological knowledge based filter is applied on the input list to remove the pathogen proteins which are unable to interact with the host proteins, and remove the host proteins which are unable to interact with the pathogen proteins, wherein the application results in generation of a second list of HPIs. Further, a domain based statistical filter is applied on the second list to remove statistically irrelevant HPIs using the positive dataset and the negative dataset, wherein the application results in generation of a set of unknown HPIs. In the next step, an extreme gradient boosting (XGBoost) model is trained using a sequence composition of interacting pairs of HPIs obtained from the positive dataset and the negative dataset (212). And finally, the set of unknown HPIs is provided as input to the trained XGBoost model to predict the interactions.

In another aspect the embodiment here provides one or more non-transitory machine readable information storage mediums comprising one or more instructions which when executed by one or more hardware processors cause predicting protein-protein interaction between a host and a pathogen. Initially, a positive dataset is collected from a first database, wherein the positive dataset contains a set of known host pathogen interactions (HPIs). Similarly, a negative dataset is collected from a second database, wherein the negative dataset contains non-interacting proteins of the host and the pathogen which are unlikely to exhibit direct physical interactions. In the next step, a cross of all possible interactions is created between a set of host proteins and a set of pathogen proteins to get an input list of host-protein interactions (HPIs). Further, a biological knowledge based filter is applied on the input list to remove the pathogen proteins which are unable to interact with the host proteins, and remove the host proteins which are unable to interact with the pathogen proteins, wherein the application results in generation of a second list of HPIs. Further, a domain based statistical filter is applied on the second list to remove statistically irrelevant HPIs using the positive dataset and the negative dataset, wherein the application results in generation of a set of unknown HPIs. In the next step, an extreme gradient boosting (XGBoost) model is trained using a sequence composition of interacting pairs of HPIs obtained from the positive dataset and the negative dataset (212). And finally, the set of unknown HPIs is provided as input to the trained XGBoost model to predict the interactions.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
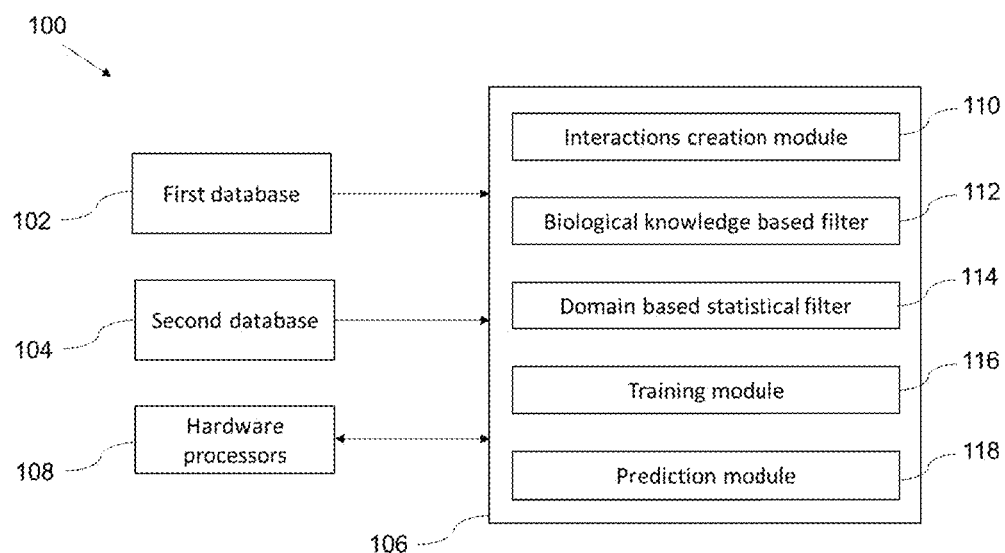
FIG. 1 shows a block diagram of a system for predicting protein-protein interaction between a host and a pathogen according to an embodiment of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

Referring now to the drawings, and more particularly to FIG. 1 through FIG. 4, where similar reference characters denote corresponding features consistently throughout the figures, there are shown preferred embodiments and these embodiments are described in the context of the following exemplary system and/or method.

According to an embodiment of the disclosure, a system 100 for predicting protein-protein interaction between a host and a pathogen is shown in the block diagram of FIG. 1. The system 100 is configured to recognize new host pathogen interactions (HPIs) to understand the mechanism of host-invasion by pathogen proteins. A detailed mechanistic idea will help in identification of druggable targets. The system 100 is using a pipeline consisting of a series of filters like biological knowledge based filter, a domain based statistical filter, followed by a sequence based machine learning method to significantly decrease the false positive rates of the predictions of HPIs. Since host-pathogen interactions are a type of protein-protein interactions, experimental training sets comprising of non-interacting protein-protein pairs can be used as negative training set. Usage of such experimentally known training sets for both positive and negative datasets significantly enhances the quality of HPI predictions.

Figure 2:
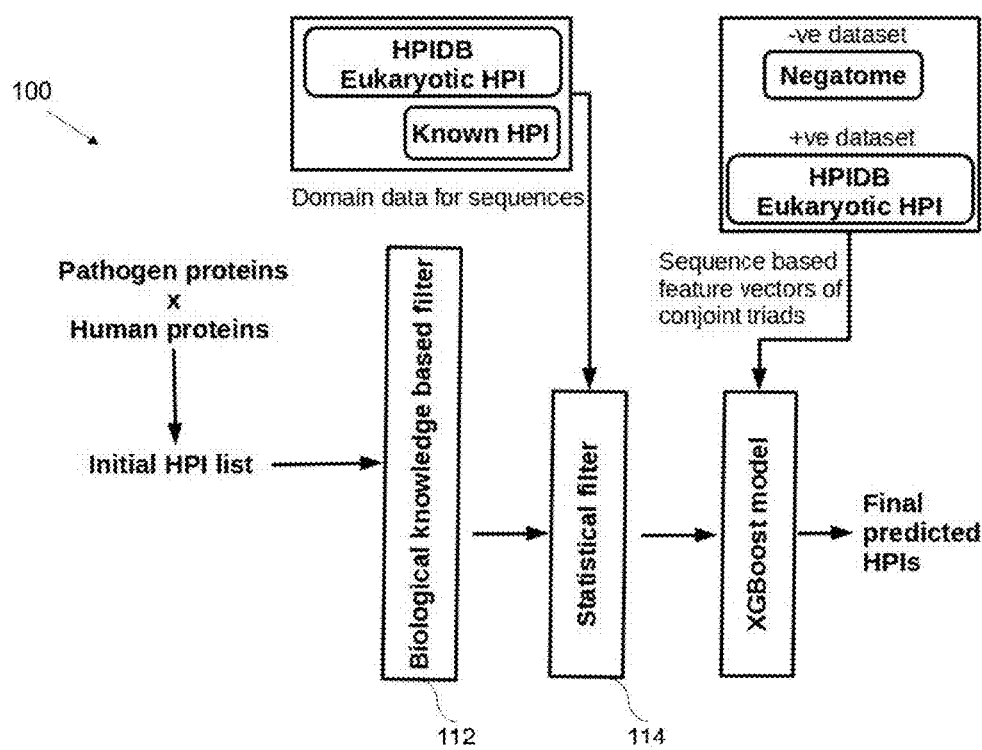
FIG. 2 shows the schematic pipeline of the system for predicting protein-protein interaction between a host and a pathogen according to an embodiment of the present disclosure.

According to an embodiment of the disclosure, the system 100 comprises a first database 102, a second database 104, a memory 106 and one or more hardware processors 108 as shown in the block diagram of FIG. 2. The one or more hardware processors 108 work in communication with the memory 106. The one or more hardware processors 108 are configured to execute a plurality of algorithms stored in the memory 106. The memory 106 further includes a plurality of modules for performing various functions. The memory 106 includes an interactions creation module 110, a biological knowledge based filter 112, a domain based statistical filter 114, a training module 116 and a prediction module 118. The memory 108 may further comprise other modules for performing certain functions.

According to an embodiment of the disclosure, the first database 102 is configured to provide a positive dataset, while the second database 104 is configured to provide a negative dataset. The positive dataset contains a set of known host pathogen interactions (HPIs). The negative dataset contains non-interacting proteins of the host and the pathogen which are unlikely to exhibit direct physical interactions. In an example, the first database 102 used is HPIDB and the second database 104 used is Negatome. It should be appreciated that the utilization of any other database is well within the scope of this disclosure.

According to an embodiment of the disclosure, the memory 106 comprises interactions creation module 110. The interactions creation module 110 is configured to create a cross of all possible interactions between a set of host proteins and a set of pathogen proteins to get an input list of host-protein interfaces (HP's). As mentioned above, HPIs between human host and eukaryotic pathogens were extracted from the first database HPIDB 3.0. The training set for non-interacting proteins which are unlikely to exhibit direct physical interaction were obtained from the Negatome. Database may also include any dataset from any source of data-generation. However the quality of this dataset will drastically impact the outcomes.

According to an embodiment of the disclosure, the memory 106 comprises the biological knowledge based filter 112 as shown in FIG. 2. The biological knowledge based filter 112 is configured to apply filter on the input list to remove the pathogen proteins which are unable to interact with the host proteins, and remove the host proteins which are unable to interact with the pathogen proteins. The application of biological knowledge based filter 112 results in the generation of a second list of HPIs. Biologically feasible interactions are only possible when both the proteins share common localization and overlapping expression profiles. Further explanation of the biological knowledge based filter 112 has been provided in detail in the later part of the disclosure with the example of pathological effects of P. falciparum.

According to an embodiment of the disclosure, the memory 106 further comprises the domain based statistical filter 114. The domain based statistical filter 114 is configured to apply filter on the second list of HPIs to remove statistically irrelevant HP Is. The application of domain based statistical filter 114 results in generation of a set of unknown HPIs.

In an example, domain information for both pathogen and human proteins was obtained from InterPro database. Domains are the fundamental biophysical units in any protein-protein interaction. Not only the domains from interacting protein pairs, but the domains of non-interacting protein pairs also provide significant information about the probability of an interaction. Unlike previous studies, which did not consider this information, we have modified a known method in the prior art to cater to this additional information. If a protein g contains a domain d and a protein h contains a domain e, then the probability of g interacting with h, $Pr\{g,h|d,e\}$, will depend on similar interactions in the training set where a domain d interacted with domain e in positive dataset ($S_{de}$) and negative dataset ($S'_{de}$). This is calculated using equation (1) where the probability of protein g to interact with protein h (where d and e are on g and h respectively):

$$Pr\{g, h \mid d, e\} = \frac{|S_{d,e}|}{|P_d||P_e| - |P_d \cap P_e|} - \frac{|S'_{d,e}|}{|P'_d||P'_e| - |P'_d \cap P'_e|} \quad (1)$$

where the frequency of domain d in the positive and negative dataset is given by Pd and P'd respectively. The possibility of d and e on same protein is corrected. All the domains on the probable interacting proteins, $M_g$ and $M_h$ are evaluated using Bayes rule that protein g interacts with protein h as shown in equation (2):

$$Pr\{I(g,h)\}=1-\Pi_{d \in M_g}\Pi_{e \in M_h}(1-Pr\{g,h|d,e\}) \quad (2)$$

Domains occurring in at least two interacting (in positive dataset) or non-interacting protein pairs (in negative dataset) were considered and interactions having a probability of more than 0.5 were considered as stringent cut-off for further analysis to remove false positives.

According to an embodiment of the disclosure, the memory 106 also comprises the training module 116. The training module 116 is configured to train an extreme gradient boosting (XGBoost) model using a sequence composition of interacting pairs of HPIs obtained from the positive dataset and the negative dataset.

A machine learning model trained with sequence compositions of pairs of known interacting proteins was used as a subsequent filter to obtain the final HP Is. It was hypothesized that each amino acid of a protein has a distinct role in HPI interaction and the interaction between two proteins can be expressed as a function of the sequence composition of the proteins. In order to reduce the computational cost, the amino acids were grouped into 7 classes based on the amino acid side chain dipoles and volumes. This approach helps to avoid sparse matrix calculations. Any three contiguous amino acids in a sequence were considered as a conjoint triad where, the neighbors of an amino acid were considered to play a significant role in the properties of the amino acid. Triads composed of three amino acids belonging to the same class can be treated identically since they can be considered to play similar roles in a PPI. The frequency of each of the triads was calculated for each protein and each protein pair was represented by a frequency vector formed by appending the triad frequencies of both the proteins. Frequency vectors of triads created from known interacting and non-interacting protein sequences were used for training the machine learning model.

According to an embodiment of the disclosure, the memory 106 comprises prediction module 118. The prediction module 118 is configured to predict the interactions using the set of unknown HPIs and the trained XGBoost model. The set of unknown HPIs are provided as input to the trained XGBoost model. Extreme gradient boosting or XGBoost is a widely acclaimed ensemble learning method that uses gradient boosted decision trees designed for speed and performance and low error rates. XGBoost uses boosting where new models are added based upon the errors made by existing models.

Figure 3A:
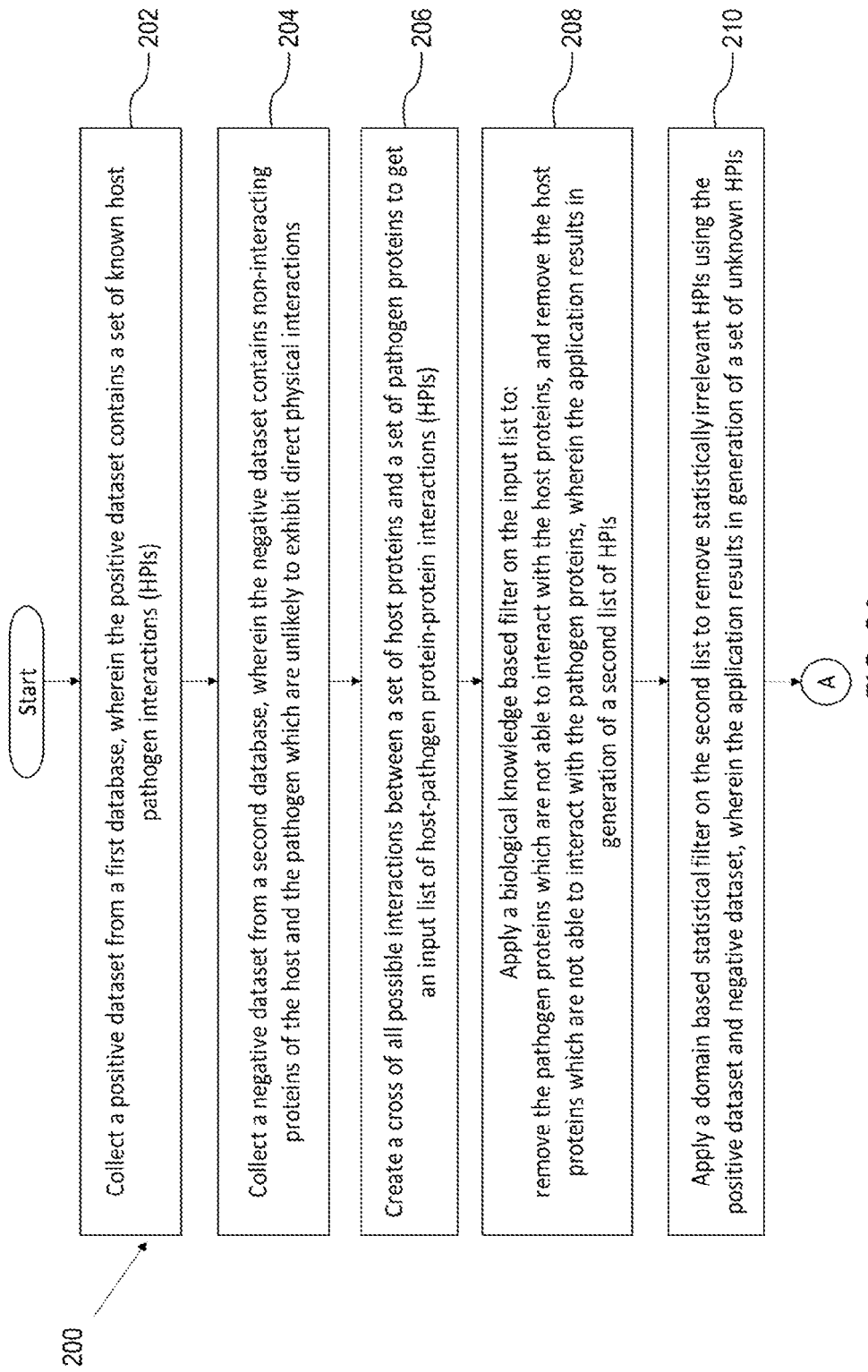
FIG. 3A-3B shows a flowchart illustrating the steps involved in predicting protein-protein interaction between a host and a pathogen according to an embodiment of the present disclosure.
Figure 3B:
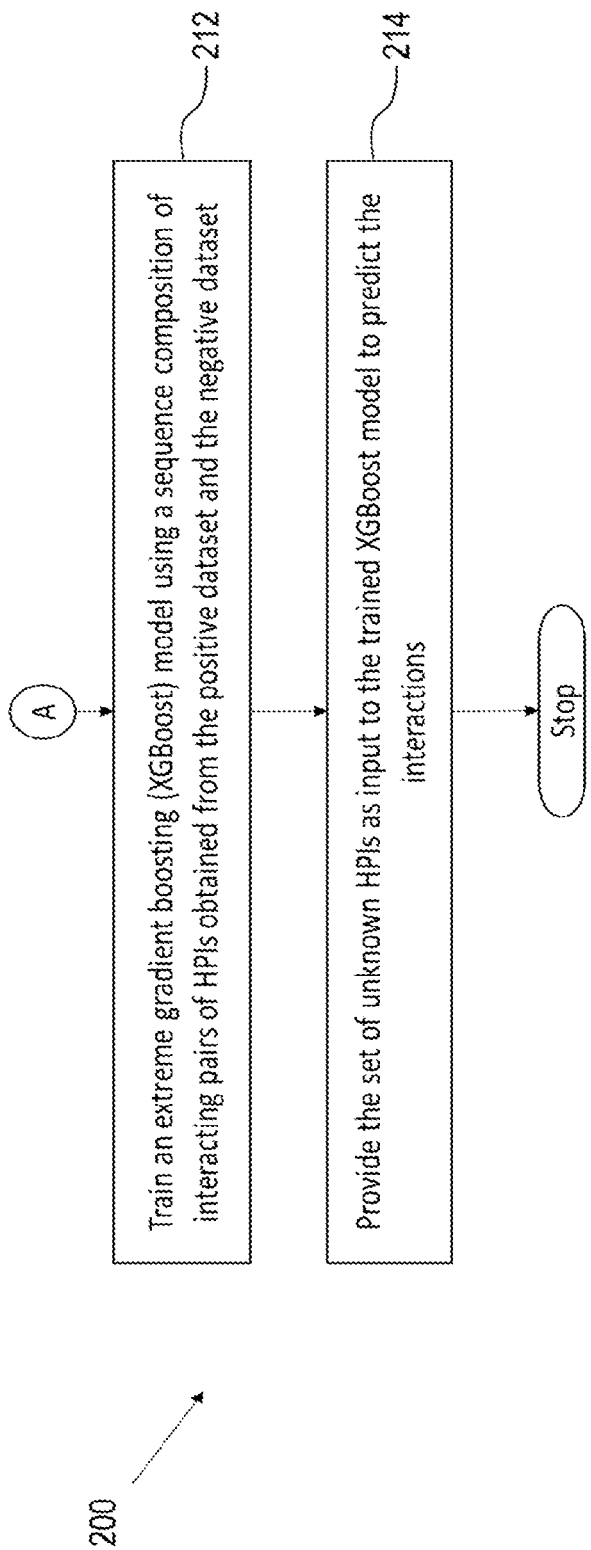

In operation, a flowchart 200 illustrating a method for predicting protein-protein interaction between the host and the pathogen is shown in flowchart of FIG. 3A-3B. Initially, at step 202, the positive dataset is collected from the first database 102. The positive dataset contains the set of known host pathogen interactions (HPIs). In an example HPIDB 3.0 is used as the first database 102. Similarly, at step 204, the negative dataset is collected from the second database 104. The negative dataset contains non-interacting proteins of the host and the pathogen which are unlikely to exhibit direct physical interactions. In an example, Negatome is used as the second database 104. At step 206, a cross of all possible interactions is created between the set of host proteins and the set of pathogen proteins to get an input list of host-protein interactions (HPIs).

At step 208, the biological knowledge based filter 112 is applied on the input list to remove the pathogen proteins which are unable to interact with the host proteins, and remove the host proteins which are unable to interact with the pathogen proteins. The application results in generation of the second list of HPIs. Biologically feasible interactions are only possible when both the proteins share common localization and overlapping expression profiles.

At step 210, the domain based statistical filter 114 is applied on the second list to remove statistically irrelevant HPIs. The application results in generation of the set of unknown HPIs. Further at step 212, the extreme gradient boosting (XGBoost) model is trained using the sequence composition of interacting pairs of HPIs obtained from the positive dataset and the negative dataset. And finally at step 214, the set of unknown HPIs are provided as input to the trained XGBoost model to predict the interactions.

According to an embodiment of the disclosure, the system 100 can also be explained with the help of following example. Data about human proteins was extracted from Uniprot database and data for P. falciparum was obtained from PlasmoDB database while pathogen expression data was collected from an RNA-seq experiment for intra-erythrocytic stages (ring, trophozoite and schizont).

Figure 4:
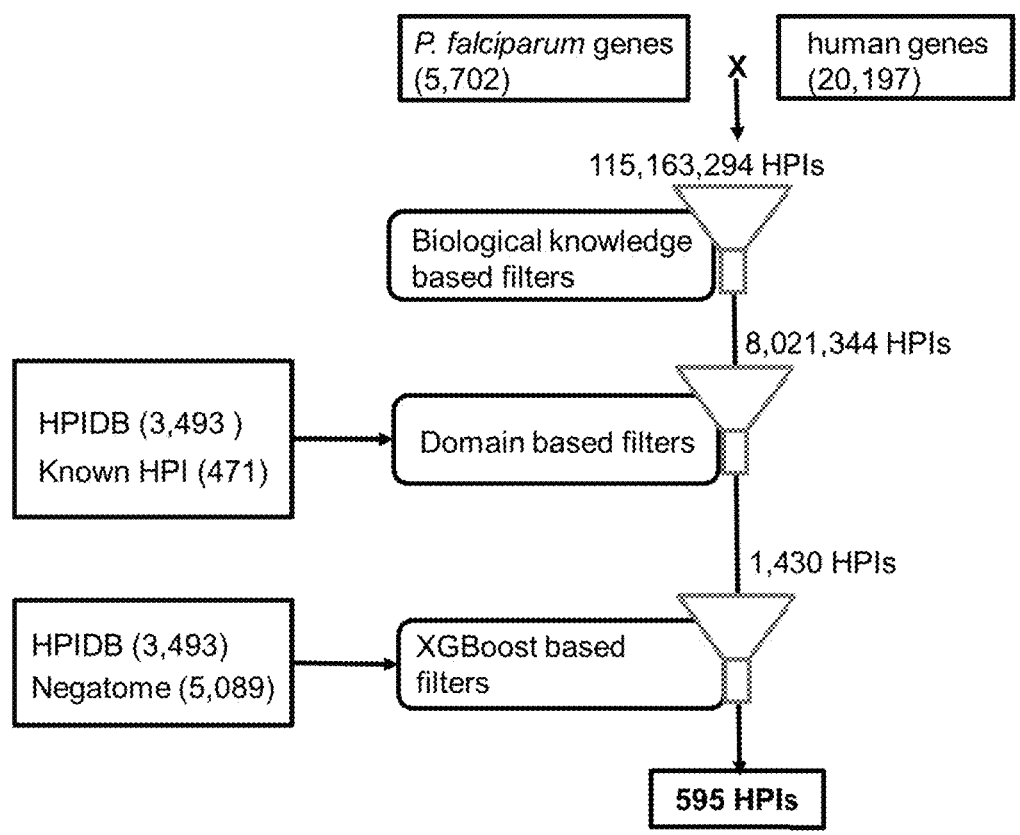
FIG. 4 shows the application of the HPI prediction pipeline using the prediction pipeline to predict HPIs involving P. falciparum proteins with proteins in human erythrocytes according to an embodiment of the present disclosure.

The HPI prediction pipeline of the present disclosure was applied on *P. falciparum* to predict unknown HPIs. An initial list comprising all human and *P. falciparum* proteins was first created. Application of biological knowledge-based filters on the initial list resulted in 1,336 *P. falciparum* proteins and 6,004 human proteins totaling 8,021,344 HPIs which were pipelined for further filtration as shown in FIG. 4. Applying the domain-based filter removed considerable number of the HPIs from the previous list and only 1,430 were passed to the final filter. The XGBoost algorithm was next applied on this list, resulting in a total of 595 HPIs. These 595 predicted HPIs consisted of 121 unique human erythrocyte proteins and 169 unique *P. falciparum* proteins. These were further analyzed to understand the importance of host-pathogen interactions.

In this particular example, following two types of biological knowledge based filters are used—Human protein filter and pathogen protein filter.

Human protein filter—Since the pathological effects of *P. falciparum* are observed during erythrocyte invasion in humans, only proteins expressed in erythrocytes were selected for further analyses. Human proteins annotated with house-keeping activities like ribosome, nucleoside binding, proteolysis, nucleic acid binding and nucleotide binding were removed. Ubiquitous proteins like ubiquitin, splicing factors, translation and transcription related proteins were also removed. Proteins related to blood coagulation, cell death, protein folding and polymerization were added to the list.

Pathogen protein filter—Erythrocyte membrane proteins (EMPs), stevors, rifins and heat shock proteins (HSPs) were considered for the subsequent analyses along with proteins related to invasion, microneme, rhoptry, transport, Maurer's clefts and proteins containing the PNEP/PEXEL export motifs. *P. falciparum* proteins localized at mitochondrion, nucleus, ribosome, gametocyte, oocyte and cytoskeleton along with proteins exhibiting helicase activity, complex formation, nuclease activity, nucleic acid-binding and nucleotide-binding were removed as they might not participate in HPIs. Proteins related to subtilisin, dense granule, haemoglobin, protein folding, polymerization and cell death were added to the list.

Further following results were obtained from the example provided in the present disclosure.

Pathogen proteins target hubs and bottlenecks in human proteome—Biological networks display scale-free properties which is robust against random attacks but suffer from complete disconnectedness during targeted attacks. Pathogens have evolved targeted attacks on human protein-protein interaction networks to disrupt proteins involved in key pathways and complexes. It was observed that 31 and 41 human proteins in the predicted HPIs are hubs and bottlenecks, respectively in the complete human proteome. These observations are in accord with previous HPI prediction methods, validating the effectiveness of this prediction method.

Predicted human proteins at various parasite stages— Peak gene expression analysis showed that predicted interactions with human proteins related to immune response, cell adhesion and signal transduction are enriched mostly in the ring stage of *P. falciparum*. Previous experimental observations indicate that cell adhesion and subsequent signal transduction is of primary importance for the successful erythrocyte invasion by *P. falciparum* merozoites. A relatively minor involvement of human stress response, transport, metabolism and cytoskeletal proteins in the initial stages of *P. falciparum* invasion was observed from predictions highlighting the known involvement of human chaperone proteins for combating heat shock during malaria and active remodeling of the actin cytoskeleton of erythrocytes.

*P. falciparum* enters the liver and then multiplies to form merozoites. Merozoites invade human red blood cell (RBC) and undergo a number of modifications through ring, trophozoite and schizont stages. In trophozoite stage, proteins related to human stress response, metabolism, transport and cytoskeleton are targeted by the pathogen proteins, supporting previous observations that the parasite is most active and undergoes exponential growth at the trophozoite stage, while human transport proteins, notably nucleoside transporter 1 (NT1), have been reported to be exploited by the pathogen to support the pathogenic metabolic pathways. In schizont stage, the parasite growth objective shifts from accelerated growth to cell division and egress. It was observed that the predicted pathogen proteins target human immune response, cell adhesion and transport proteins which a previous study showed to be essential to facilitate erythrocyte sequestration in vascular endothelium and to support its next life cycle after egress. These observations indicating the biological relevance of the predictions validate the HPI prediction method.

Several pathogen proteins target human cytoskeletal proteins—The malarial parasite inflicts major perturbations to the host erythrocyte, remodeling the erythrocyte cytoskeleton in the process. Human proteins in the predicted HPIs related to erythrocyte cytoskeletal components were chosen to analyze the predicted novel HPIs. A total of 14 erythrocyte cytoskeletal proteins were targeted by 19 *P. falciparum* proteins in the present HPI predictions. These were used along with known HPIs to construct a network of 56 nodes providing a holistic understanding of the erythrocyte cytoskeleton targets of *P. falciparum*.

The stabilization of human cytoskeletal proteins by the parasite heat shock proteins during periodic febrile episodes of malaria is well known from experimental studies. In the present disclosure, it was observed that the predicted HSPs interact with many of the human spectrins and microtubule-associated proteins of RP/EB family (MARE). The interaction of invasion-related proteins like merozoite surface protein family (MSP) and cytoadherence-linked asexual protein family (CLAG), with cytoskeleton components are important for pathogenesis. One such human protein that has been targeted is periplakin (PEPL), which is a component of the cornified envelope of keratinocytes and probably links the cornified erythrocyte envelope to desmosomes, cell-cell adhesion junction components. PEPL is known to have key roles in protein kinase B (PKB) mediated cell signaling, ligand binding, receptor-mediated endocytosis and immune response and connects the cytoplasmic domains of cellular adhesion complexes to the cytoskeleton. Hence, PEPL might be one of the key targets for remodeling of erythrocyte cytoskeleton after formation of the tight junction complex during *P. falciparum* invasion.

Other Biologically important HPIs—In the present disclosure, it was found that 54 human immune response related proteins being targeted by 86 *P. falciparum* proteins which includes exported and invasion-related proteins of *P. falciparum*. Evading human immune response is an important biological event during malaria. Two of such interesting HPIs have been discussed below:

Clp proteases modulate signaling and immune response pathways in human—The predicted interactions between *P. falciparum* Clp proteases and chaperones with the Coxsackie virus and adenovirus receptor (CAR) of the junctional adhesion protein family along with Lyn kinase (LYN) and Btk kinase (BTK) of the tyrosine protein kinase family are of particular interest. CAR protein is a well-recognized key mediator of cell-cell adhesion and acts as a regulator of junction dynamics through association with adaptor proteins, cytoskeletal remodeling and additional indirect signaling pathways. LYN is a mediator of inflammatory response and is also an activator of the MAP kinase cascade and has been shown to have an antiapoptotic effect in response to genotoxic stress and heat shock. BTK is from the receptor tyrosine kinase family with similar functions interacting with the Clp proteases and chaperones. Further, LYN and BTK belong to the Src kinase family which are activated during heat shock to prevent irrelevant apoptosis. These HPIs highlight the importance of pathogen Clp proteases in pathogen survival.

PfEMP1 participates in immunomodulation—Erythrocyte membrane protein (PfEMP1) is the major virulent protein of *P. falciparum* and is the primary component of the surface knobs on the infected erythrocytes. The HPI predictions include 120 HPIs between PfEMP1s and several human proteins including CAR, immunoglobulin kappa (KV105, KV311, KVD11), butyrophilins (BT3A2, BT2A2, BT3A3), erythroid membrane-associated protein (ERMAP), syndecan-2 (SDC2) and basigin (BASI). Interaction of PfEMP1 with these proteins would involve an enhancement of the cytoadhesion phenotype attributed to the PfEMP1 family, leading to the sequestration of infected RBCs. The HPI predictions involving interaction of PfEMP1 with immune response related proteins suggest the role of the parasite in modulating the human immune response pathways to enhance survival and to evade recognition by the human immune system. These novel interactions might be important for understanding malaria pathogenesis.

The embodiments of the present disclosure herein solve the problems of the high false positive rate during the prediction of HPIs. The disclosure provides a method and system for predicting protein-protein interaction between a host and a pathogen.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method for predicting protein-protein interaction between a host and a pathogen, the method comprising:
    collecting, via the one or more hardware processors, a positive dataset from a first database, wherein the positive dataset contains a set of known host-pathogen interactions (HPIs);
    collecting, via the one or more hardware processors, a negative dataset from a second database, wherein the negative dataset contains non-interacting proteins of the host and the pathogen;
    creating, via the one or more hardware processors, a cross of all possible interactions between a set of host proteins and a set of pathogen proteins to get an input list of host-pathogen interactions (HPIs);
    applying, via the one or more hardware processors, a biological knowledge based filter on the input list to:
        remove the pathogen proteins which are unable to interact with the host proteins, and
        remove the host proteins which are unable to interact with the pathogen proteins, wherein the application of biological knowledge based filter results in generation of a second list of HPIs;
    applying, via the one or more hardware processors, a domain based statistical filter on the second list to remove statistically irrelevant HPIs using the positive dataset and the negative dataset, wherein the application of domain based statistical filter results in generation of a set of unknown HPIs;
    training, via the one or more hardware processors, an extreme gradient boosting (XGBoost) model using a sequence composition of interacting pairs of HPIs obtained from the positive dataset and the negative dataset; and
    providing, via the one or more hardware processors, the set of unknown HPIs as input to the trained XGBoost model to predict the interactions.

2. The method of claim 1, wherein the host is a human and the pathogen is eukaryotic pathogens.

3. The method of claim 1, wherein the XGBoost model is trained with a 3-fold cross validation.

4. The method of claim 1, wherein the domain based statistical filter captures a frequency of a specific pair of domain interactions from interacting protein pairs as well as non-interacting protein.

5. The method of claim 1, wherein the first database is Host—Pathogen Interaction Database (HPIDB) and the second database is Negatome.

6. The method of claim 1, wherein the step of applying a biological knowledge based filter further comprises removing host and pathogen proteins annotated with tissue or cellular localization and activities not related to host-pathogen interactions.

7. The method of claim 1, further comprising getting information related to the domain based statistical filter from Uniprot database.

8. The method of claim 1, further comprising using frequency vectors of triads created from known interacting and non-interacting protein sequences for training the XGBoost model.

9. A system for predicting protein-protein interaction between a host and a pathogen, the system comprises:
  a first database for providing a positive dataset, wherein the positive dataset contains a set of known host pathogen interactions (HPIs);
  a second database for providing a negative dataset, wherein the negative dataset contains non-interacting proteins of the host and the pathogen;
  one or more hardware processors;
  a memory in communication with the one or more hardware processors, the memory further comprising:
  an interactions creation module for creating a cross of all possible interactions between a set of host proteins and a set of pathogen proteins to get an input list of host-protein interfaces (HPIs);
  a biological knowledge based filter for applying filter on the input list to:
    remove the pathogen proteins which are unable to interact with the host proteins, and
    remove the host proteins which are unable to interact with the pathogen proteins, wherein the application of biological knowledge based filter results in generation of a second list of HPIs;
  a domain based statistical filter for applying filter on the second list to remove statistically irrelevant HPIs using the positive dataset and the negative dataset, wherein the application of domain based statistical filter results in generation of a set of unknown HPIs;
  a training module for training an extreme gradient boosting (XGBoost) model using a sequence composition of interacting pairs of HPIs obtained from the positive dataset and the negative dataset; and
  a prediction module for predicting the interactions using the set of unknown HPIs and the trained XGBoost model, wherein the set of unknown HPIs are provided as input to the trained XGBoost model.

10. One or more non-transitory machine readable information storage mediums comprising one or more instructions which when executed by one or more hardware processors cause managing a plurality of events, the instructions cause:
  collecting a positive dataset from a first database, wherein the positive dataset contains a set of known host-pathogen interactions (HPIs);
  collecting a negative dataset from a second database, wherein the negative dataset contains non-interacting proteins of the host and the pathogen;
  creating a cross of all possible interactions between a set of host proteins and a set of pathogen proteins to get an input list of host-pathogen interactions (HPIs);
  applying a biological knowledge based filter on the input list to:
    remove the pathogen proteins which are unable to interact with the host proteins, and
    remove the host proteins which are unable to interact with the pathogen proteins, wherein the application of biological knowledge based filter results in generation of a second list of HPIs;
  applying a domain based statistical filter on the second list to remove statistically irrelevant HPIs using the positive dataset and the negative dataset, wherein the application of domain based statistical filter results in generation of a set of unknown HPIs;
  training an extreme gradient boosting (XGBoost) model using a sequence composition of interacting pairs of HPIs obtained from the positive dataset and the negative dataset; and
  providing the set of unknown HPIs as input to the trained XGBoost model to predict the interactions.

* * * * *